(12) United States Patent
Gimeno Asin et al.

(10) Patent No.: US 11,576,992 B2
(45) Date of Patent: Feb. 14, 2023

(54) METHOD AND SYSTEM FOR GENERATING A FRAGRANCE

(71) Applicant: BSH HAUSGERAETE GMBH, Munich (DE)

(72) Inventors: Manuel Gimeno Asin, Saragossa (ES); Jakub Jan Jedlinski, Neubiberg (DE); Hugo Lasala Alonso, Saragossa (ES); Alvaro Suarez Iribarne, Barcelona (ES)

(73) Assignee: BSH Hausgeraete GmbH, Munich (DE)

( * ) Notice: Subject to any disclaimer, the term of this patent is extended or adjusted under 35 U.S.C. 154(b) by 566 days.

(21) Appl. No.: 16/497,785

(22) PCT Filed: Mar. 29, 2018

(86) PCT No.: PCT/EP2018/058260
§ 371 (c)(1),
(2) Date: Sep. 25, 2019

(87) PCT Pub. No.: WO2018/178320
PCT Pub. Date: Oct. 4, 2018

(65) Prior Publication Data
US 2021/0100923 A1    Apr. 8, 2021

(30) Foreign Application Priority Data

Mar. 29, 2017 (EP) .................... 17382159
Mar. 29, 2017 (EP) .................... 17382160
(Continued)

(51) Int. Cl.
*A61L 9/12* (2006.01)
*B01F 33/84* (2022.01)
*A61Q 13/00* (2006.01)

(52) U.S. Cl.
CPC .......... *A61L 9/125* (2013.01); *B01F 33/8442* (2022.01); *A61L 2209/111* (2013.01);
(Continued)

(58) Field of Classification Search
CPC .............. A61L 9/125; A61L 2209/111; A61L 2209/133; A61L 9/035; A61L 2209/11;
(Continued)

(56) References Cited

U.S. PATENT DOCUMENTS

2006/0293871 A1    12/2006  Fazzio et al.
2011/0295400 A1*   12/2011  Samain .............. G06Q 50/04
                                                  700/97
(Continued)

FOREIGN PATENT DOCUMENTS

EP    1245269 A1    10/2002
EP    2252542       11/2010
(Continued)

OTHER PUBLICATIONS

International Search Report and Written Opinion dated Jun. 11, 2018 for PCT Application No. PCT/EP2018/058260, 16 pages.
(Continued)

*Primary Examiner* — Sean E Conley
*Assistant Examiner* — Brendan A Hensel
(74) *Attorney, Agent, or Firm* — Laurence A. Greenberg; Werner H. Stemer; Ralph E. Locher

(57) ABSTRACT

A method and a system for generating a fragrance (also referred to herein as perfume) are disclosed. A method may comprise providing a perfume blender machine (100) and cartridges (102) for storing liquid olfactory ingredients (112), the machine comprising dispensing means to dispense olfactory ingredients (112) from the cartridges (102) for generating a fragrance (114); controlling the dispensing means to generate a fragrance (114) based on instructions
(Continued)

given by a user on the liquid olfactory ingredients (112) to be blended and the quantity of each; and generating a recipe with the information of the ingredients (112) and their respective quantities which have been used to generate the fragrance.

10 Claims, 3 Drawing Sheets

(30) Foreign Application Priority Data

Mar. 29, 2017 (ES) ................................ ES201730467
Mar. 29, 2017 (ES) ................................ ES201730469

(52) U.S. Cl.
  CPC .......... *A61L 2209/133* (2013.01); *A61Q 13/00* (2013.01); *B01F 33/846* (2022.01)
(58) Field of Classification Search
  CPC ........... A61L 2209/134; B01F 33/8442; B01F 33/846; A61Q 13/00
  See application file for complete search history.

(56) References Cited

U.S. PATENT DOCUMENTS

| | | |
|---|---|---|
| 2012/0005222 A1 | 1/2012 | Bhagwan et al. |
| 2012/0128240 A1 | 5/2012 | Rothschild |
| 2014/0288700 A1 | 9/2014 | Peters et al. |
| 2021/0128868 A1* | 5/2021 | Matsumoto ....... H04M 1/72403 |

FOREIGN PATENT DOCUMENTS

| | | |
|---|---|---|
| EP | 2433656 A1 | 3/2012 |
| WO | WO 2010/058381 A1 | 5/2010 |
| WO | WO 2011/106889 A1 | 9/2011 |
| WO | WO 2017/103634 A1 | 6/2017 |

OTHER PUBLICATIONS

ANONYMOUS: "Fragrance pyramid" Oct. 3, 2014; retrieved from the internet on Aug. 30, 2017; URL:http://www.expedition-perfumes.com/files/cto_layout/bilder/duftpyramiede_arctic_en.jpg, Figure 1, XP055402305, 1 page.

* cited by examiner

METHOD AND SYSTEM FOR GENERATING A FRAGRANCE

This application is a 35 U.S.C. 371 filing of International Application No. PCT/EP2018/058260 filed Mar. 29, 2018, which claims priority to EP17382159.6 filed Mar. 29, 2017, EP 17382160.4 filed Mar. 29, 2017, ES P201730467 filed Mar. 29, 2017, and ES P201730469 filed Mar. 29, 2017, all of which are incorporated verbatim herein by reference in their entirety, including the specification, drawing, and the claims.

The present document is directed at a method and a system for generating a fragrance (also referred to herein as perfume).

There is an increasing demand for creating individualized fragrances or perfumes for special occasions and/or for different moods. In this context a perfume blender machine may be provided, which enables a user to create an individual fragrance or perfume based on a set of olfactory ingredients.

The present document is directed to the technical problem of enabling a user to generate an individualized fragrance or perfume in a comfortable and efficient manner.

The present document is also directed at the technical problem of enabling a user and a perfume blender machine to determine the composition of an individual fragrance or perfume in a comfortable and precise manner.

Furthermore, the present document is also directed at the technical problem of enabling a user to experiment with new, personalized fragrances and perfumes in a comfortable and precise manner.

The technical problems are at least partly solved by the independent claims. Preferable embodiments and examples are described within the dependent claims, within the description and within the accompanying drawing.

According to a first aspect, a method for generating a fragrance is provided. The method comprises providing a perfume blender machine and a plurality of cartridges for storing a corresponding plurality of liquid olfactory ingredients, the blender machine comprising dispensing means configured to dispense one or more olfactory ingredients from the plurality of cartridges for generating a fragrance; controlling the dispensing means to generate a fragrance based on instructions inputted by a user on the liquid olfactory ingredients to be blended and the quantity of each; recording the information regarding the plurality of liquid olfactory ingredients and their respective quantities which have been used to generate the fragrance; and generating a recipe of the fragrance with the recorded information.

According to another aspect, a method for generating a fragrance is provided, comprising: providing a perfume blender machine having a plurality of cartridges for storing a corresponding plurality of liquid olfactory ingredients and provided with communication means configured to provide information regarding the olfactory ingredient comprised within the cartridge in a machine readable manner; dispensing means configured to dispense one or more olfactory ingredients from the plurality of cartridges for generating a fragrance; reading means configured to interact with the communication means of the plurality of cartridges for capturing information regarding the plurality of olfactory ingredients; and a control unit. The method also comprises determining the information regarding the plurality of olfactory ingredients; determining a recipe for a fragrance based on the information regarding the plurality of liquid olfactory ingredients and their respective quantities, and based on instructions given by a user; controlling the dispensing means to generate the fragrance based on the recipe; and encoding within a recipe the information regarding the plurality of liquid olfactory ingredients and their respective quantities which have been used to generate the fragrance.

The generated recipe may be encoded for example in a machine readable code, and/or a pictorial code from which a user may visually derive easily the main olfactory features of the fragrance.

According to another aspect the present disclosure provides a perfume blender machine or system, configured to generate a fragrance, comprising: dispensing means configured to dispense one or more olfactory ingredients from a plurality of cartridges for storing a corresponding plurality of liquid olfactory ingredients, the cartridges being provided with communication means configured to provide information regarding the olfactory ingredient comprised within the cartridge in a machine readable manner; reading means configured to interact with the communication means of the plurality of cartridges for capturing information regarding the plurality of olfactory ingredients; and a control unit configured to: determine and provide to a user the information regarding the plurality of olfactory ingredients present in the machine; receive instructions by the user to generate a fragrance blending the plurality of liquid olfactory ingredients in respective quantities; control the dispensing means to generate the fragrance based on the received user instructions; and encode within a recipe the information regarding the plurality of liquid olfactory ingredients and their respective quantities which have been used to generate the fragrance.

Methods and systems according to the above aspects allow a user to experiment with new, personalized fragrances, which he/she can mix in the blender machine by inputting instructions on the ingredients and amounts to use, and obtain an encoded recipe of the fragrance obtained in each case. The encoded recipe may be e.g. stored in a memory in the perfume blender machine, or uploaded via a communication unit to a recipe database of a server, and it may be recalled at a later time to be reproduced or modified, or it may be shared with other users, etc.

This allows the user to experiment and share his/her personalized fragrances with other users, in a comfortable and precise manner.

In methods as disclosed, encoding within a recipe the information regarding the plurality of liquid olfactory ingredients and their respective quantities which have been used to generate the fragrance may comprise generating and storing a pictorial code representing the composition of the fragrance. Such a pictorial code may be as in any of the embodiments and examples presented in this disclosure.

A machine readable code may be associated with the pictorial code, such that the recipe may be both readily understood by a user and machine-read. Furthermore, the pictorial code itself may be readable by a suitable image-processing device.

In a system or machine such as disclosed, the control unit may be configured to search for a recipe within a recipe database using the identifiers of the plurality of olfactory ingredients present in the machine, and/or it may be configured to determine additional information regarding an additional olfactory ingredient comprised in one or more cartridges that are not present in the machine, and to determine a recipe based on the additional information. For example, it may search for additional information and recipes in a memory of the machine, based on previous use data or on downloaded data.

The control unit may communicate with an external server via a communication unit of the machine to search for a recipe. For example, it may search for a recipe in a recipe database or in a user profile database (which records e.g. the cartridges purchased by a user, or cartridges of fragrances related to user preferences) in a server.

According to an aspect of the invention a cartridge or container for storing an olfactory ingredient for a fragrance or perfume is described. The cartridge may be configured to store a pre-determined quantity (e.g. 5, 10 or 20 milliliters) of an olfactory ingredient (e.g. a liquid having a specific scent or smell). The cartridge comprises communication means which are configured to provide information regarding the olfactory ingredient comprised within the cartridge in a machine readable manner. By way of example, the communication means may comprise a machine readable code (e.g. a barcode or a QR (Quick Response) code, an RFID (Radio Frequency Identification) tag and/or an NFC (Near Field Communication) chip. By providing a cartridge with communication means, the cartridge may be used (e.g. within a perfume blender machine) for generating an individualized fragrance in a comfortable and efficient manner.

The communication means may be configured to provide information regarding a level of the olfactory ingredient comprised within the cartridge in a machine readable manner. By way of example, the level of the olfactory ingredient (i.e. the remaining quantity of the olfactory ingredient within the cartridge) may be determined by a perfume blender machine, when using the cartridge. The level of the olfactory ingredient can be measured by the perfume blender by means of optic sensors and/or magnetic sensors and/or electronic sensors that directly identify the remaining level inside the cartridge, for such a purpose the cartridge can also be configured with moving parts (i.e: plunger pushed by the perfume blender, and/or floating elements) that can be tracked by sensors integrated in the perfume blender. Data regarding the level of the olfactory ingredient may then be stored within the communication means, and may be read by out an appropriate reading unit. By doing this, the comfort for generating individualized fragrances may be further increased.

The information regarding the olfactory ingredient may comprise an identifier which is configured to identify the olfactory ingredient from a pre-determined set of olfactory ingredients in an unambiguous and/or bijective manner. By way of example, a standardized set of olfactory ingredients may be provided (e.g. 50, 100 or more different olfactory ingredients). An identifier (e.g. a code comprising one or more numbers and/or one or more letters) may be assigned to each of the olfactory ingredients, wherein the identifier may be such that the identifier uniquely identifies the olfactory ingredient from the standardized set of olfactory ingredients. The use of unique identifiers for different olfactory ingredients enables a reliable and comfortable generation of individualized fragrances.

The communication means may be configured to provide a wireless communication interface with a corresponding reading unit over a certain communication range. In other words, the communication means may be such that the information regarding the olfactory ingredient (e.g. the identifier of the olfactory ingredient) may be captured over a certain communication range. The communication rage may be 1, 5 or more meters. By providing a relatively large communication range, the comfort for generating individualized fragrances may be increased.

According to a further aspect of the invention a system (notably a perfume blender machine) for generating a perfume or fragrance from a set of olfactory ingredients is described. The system may be implemented as a household appliance. In particular, the system may be configured to be placed within a bathroom, a dressing room or a bedroom. The system comprises a plurality of containers or cartridges for a corresponding plurality of olfactory ingredients. The different olfactory ingredients may be different liquids with different smells or scents. Furthermore, the system or the cartridges comprise dispensing means configured to dispense one or more (selected) olfactory ingredients from the plurality of containers or cartridges for generating a portion of a perfume or fragrance. The plurality of cartridges may be configured as described in the present document. In particular, the cartridges may at least partially comprise communication means for providing information regarding the respective olfactory ingredients.

Furthermore, the system comprises reading means (e.g. a camera, an RFID reader and/or an NFC chip reader) which are configured to interact with the communication means of the plurality of cartridges for capturing information regarding the plurality of olfactory ingredients. By way of example, identifiers of the plurality of olfactory ingredients may be determined using the reading means.

In addition, the system comprises a control unit (e.g. a microcontroller). The control unit may be configured to determine information regarding the plurality of olfactory ingredients using the reading unit of the system. In particular, the identifiers of the available olfactory ingredients may be determined. Furthermore, the available quantity of each olfactory ingredient may be determined.

The control unit may be further configured to determine a recipe for a fragrance based on the information regarding the plurality of olfactory ingredients. In particular, the control unit may be configured to determine identifiers for the plurality of olfactory ingredients and search for an appropriate recipe within a recipe database using the identifiers. Alternatively or in addition, the control unit may be configured to communicate with an external server via a communication unit (e.g. via a WLAN, Wireless Local Area Network, communication unit) of the system for determining the recipe for the fragrance.

The control unit may then control the dispensing means to generate the fragrance based on the recipe. Hence, the system may be configured to generating an individualized fragrance in an efficient and comfortable manner.

The reading means may exhibit a communication range for capturing data from the communication means of a cartridge, wherein the communication range goes beyond a dimension of the system (notably of the perfume blender machine). In other words, the reading means may be configured to capture information from communication means of one or more cartridges which are not placed within the system. The control unit may then be configured to determine additional information regarding an additional olfactory ingredient comprised in one or more cartridges that are not placed within the system (e.g. which are placed within the room that the system is placed in).

Furthermore, the control unit may be configured to determine a proposal for a recipe based on the additional information. The proposal may be output on a user interface of the system. The user may then be requested to place the one or more cartridges which are required for generating the fragrance described by the recipe into the system. By providing reading means and communication means with an extended communication range, the comfort for generating a fragrance may be increased further.

According to another aspect of the invention, an electronic device (e.g. a smartphone or portable computing device) configured to determine information regarding an olfactory ingredient of a cartridge is described. The electronic device comprises reading means which are configured to interact with the communication means of the cartridge for determining an identifier of the olfactory ingredient. Furthermore, the electronic device comprises a communication unit which is configured to communicate with an external server in order to determine information regarding the olfactory ingredient based on the identifier. By way of example, one or more recipes for fragrances comprising the identified olfactory ingredient may be determined.

According to a further aspect of the invention, a server comprising a recipe database for fragrances is described. The server is configured to receive a request regarding a recipe for fragrance from an electronic device and/or from a system for generating a fragrance. The request comprises the identifiers of one or more (typically two or more) olfactory ingredients which should be used within the recipe. The server may be configured to determine one or more recipes from the recipe database based on the request. In particular, one or more recipes may be determined, such that each of the one or more recipes comprises the one or more olfactory ingredients identified within the request. The server may be further configured to provide information regarding the one or more recipes back to the electronic device and/or to the system for generating a fragrance. In particular, the one or more recipes may be sent to the electronic device or to the system for generating a fragrance. A recipe for a fragrance may indicate the identifiers of one or more (typically two or more) olfactory ingredients which should be mixed for generating the fragrance. Furthermore, the recipe may indicate the quantities of the one or more olfactory ingredients which should be mixed for generating the fragrance.

According to another aspect of the invention a method for determining the composition of a fragrance or perfume from image date of a pictorial code is described. The method may be executed by an electronic device (e.g. a smartphone) for informing a user about the one or more olfactory ingredients that are comprised within the fragrance or perfume. Furthermore, the method may be executed by a machine or system for generating a specific portion of a fragrance or perfume (e.g. a few milliliters).

The pictorial code comprises one or more (typically two or more) differently coloured regions and one or more (typically two or more) symbols within the differently coloured regions. In particular, the code may have a total dimension or size of a particular form (e.g. a circular form). By way of example, the code may have the form of a wheel, wherein the wheel may be segmented into different regions. Each segment or region may cover a certain angular range of the wheel. The total dimension of the pictorial code may be subdivided into different regions, wherein the different regions may be associated with different colours. In particular, the symbols (or logos or icons) within the different regions may have different colours. As such, the pictorial code comprises colour information in combination with symbolic information. The colour of a region or symbol may be indicative of a chord, an accord or a category of aromas. Furthermore, a symbol (possibly in combination with the colour of the symbol) may be indicative of an aroma or a note. Alternatively or in addition, the colour of a region or symbol may be indicative of a family or cluster of olfactory ingredients. Furthermore, a symbol may be indicative of a subfamily or subcluster of olfactory ingredients.

The method comprises determining the colour of the one or more differently coloured regions based on the image data. In particular, image processing tools may be used to partition an image of the pictorial code into different regions with different colours. Furthermore, the method comprises detecting the one or more symbols based on the image data. In particular, image processing tools such as symbol recognition techniques may be used to analyze an image of the pictorial code for identifying the one or more symbols represented within the pictorial code.

In addition, the method comprises determining at least one ingredient of the fragrance or perfume based on the colour of the one or more differently coloured regions and based on the one or more symbols. For this purpose, a pre-determined list of symbols and a pre-determined list of colours may be provided. Furthermore, it may be determined which one or more colours of the pre-determined list of colours and which one or more symbols of the pre-determined list of symbols are comprised within the pictorial code.

The pre-determined list of colours and the pre-determined list of symbols may be associated with a pre-determined set of olfactory ingredients. In particular, a classifier (e.g. a lookup table) may be provided which assigns a combination of one or more symbols and of one or more colours to a combination of one or more ingredients. Hence, using the colour of the one or more regions and using the one or more symbols, a particular combination of one or more ingredients may be determined. In particular, one or more ingredients may be selected from the pre-determined set of olfactory ingredients.

Hence, an accurate and efficient method for determining the ingredients of a fragrance or perfume is provided. At the same time, the use of colours and symbols provides a descriptive code which may be interpreted by a person in an intuitive and comfortable manner.

The pictorial code may comprise additional information regarding the composition of a fragrance or perfume. In particular,
- the size of the one or more regions;
- the size of the one of more symbols;
- the quantity or number of the one or more symbols; and/or
- the location of the one or more symbols within the pictorial code;

may be used for providing additional information regarding the composition of a fragrance or perfume. In particular, additional information may be used for determining the quantity of the at least one ingredient of a fragrance or perfume.

The method may comprise determining, based on the image data, relative sizes or dimensions of the one or more differently coloured regions within the pictorial code. The quantity of the at least one ingredient may then be determined based on the relative sizes of the one or more differently coloured regions.

Alternatively or in addition, the method may comprise determining, based on the image data, a characteristic of a symbol. The characteristic of a symbol may comprise a size of the symbol, a quantity or number of the same symbol and/or a position of the symbol within the pictorial code. The quantity of the at least one ingredient may then be determined based on the characteristic of the symbol. By way of example, a pictorial code may comprise a particular symbol several times. The number of representations of the symbol within the pictorial code may then indicate the quantity of a particular ingredient which is associated with this symbol.

Hence, the composition of a fragrance or perfume may be determined in a precise manner.

According to a further aspect of the invention a pictorial code for describing the composition of a fragrance or perfume comprising one or more olfactory ingredients is described. The pictorial code comprises one or more differently coloured regions and one or more symbols within the differently coloured regions. In particular, the differently coloured regions may be formed or defined by differently coloured symbols. By way of example, in a first region one or more symbols may be coloured with a first colour and in a second region one or more symbols may be coloured with a second colour.

The colour of the one or more differently coloured regions and the one or more symbols are indicative of the one or more olfactory ingredients of the fragrance or perfume. In other words, the pictorial code is such that the colour of the one or more differently coloured regions and the one or more symbols may be used to determine the one or more olfactory ingredients of the fragrance or perfume. As such a pictorial code for describing the composition of a fragrance or perfume is provided, wherein the pictorial code enables a system, e.g. a perfume blender machine, to determine the one or more olfactory ingredients of a fragrance or perfume in a precise manner and wherein the pictorial code enables a user to intuitively estimate the one or more olfactory ingredients of a fragrance or perfume.

As indicated above, the pictorial code typically exhibits a total size. A relative size of the one or more differently coloured regions may be indicative of a quantity of the one or more olfactory ingredients of the fragrance or perfume. Hence, the pictorial code may also be used for indicating the quantities of the one or more olfactory ingredients of a fragrance or perfume.

A symbol of the pictorial code typically comprises a pictorial representation of an object. Example objects are a fruit, a plant, a vegetable, a flower, an animal, a monument, a building, a vehicle, etc. The object which is represented by a symbol may be associated with a particular ingredient or scent. In particular, the object may be such that the object triggers a user to make an association with a particular ingredient or scent. The association between objects and ingredients or scents may be determined in the context of perceptual experiments using a test group of user.

Different associations may be provided for different test groups (e.g. for people from different cultural groups). As such, the pictorial code may be adapted for different groups of people (e.g. for different countries).

The one or more olfactory ingredients of the fragrance or perfume that is described by the pictorial code may then comprise at least one olfactory ingredient with the particular scent or smell that is associated with the object represented by a symbol of the pictorial code. By doing this, the pictorial code enables a user to determine the combination of ingredients in an intuitive manner.

The pictorial code may comprise a number field associated with a first symbol of the one or more symbols. By way of example, a first symbol may include a number field, wherein the number field indicates a certain number. The number field (i.e. the number within the number field) may be indicative of the quantity of at least a first olfactory ingredient of the one or more olfactory ingredients of the fragrance or perfume, wherein the first olfactory ingredient is associated with the first symbol. By adding numeric information to the pictorial code, the quantities of the one or more olfactory ingredients of a fragrance or perfume may be determined in a precise manner.

According to a further aspect of the invention a system (notably a perfume blender machine) for generating a fragrance or perfume from a set of olfactory ingredients is described. The system may be implemented as a household appliance. In particular, the system may be configured to be placed within a bathroom, a dressing room or a bedroom. The system comprises a plurality of containers for a corresponding plurality of olfactory ingredients. The different olfactory ingredients may be different liquids with different scents or smell. Furthermore, the system comprises dispensing means configured to dispense one or more (selected) olfactory ingredients from the plurality of containers for generating a portion of a fragrance or perfume.

In addition, the system comprises a control unit. The control unit is configured to determine image data of a pictorial code describing the composition of a fragrance or perfume. The image data may be collected from a data base which stores image data for different pictorial codes regarding different fragrances or perfumes. Alternatively or in addition, the system may comprise or may be coupled to a camera which is configured to capture image data regarding a pictorial code. The pictorial code may be indicative of the one or more ingredients of a fragrance or perfume and possibly of the (relative) quantities of the one or more ingredients.

The control unit is further configured to determine the colour of one or more differently coloured regions of the pictorial code, based on the image data. In addition, the control unit is configured to detect one or more symbols represented within the pictorial code, based on the image data. The control unit may then determine at least one ingredient from the plurality of ingredients, based on the colour of the one or more differently coloured regions and based on the one or more symbols. In addition, the control unit may be configured to control the dispensing means to dispense the at least one ingredient from the corresponding at least one container of the system.

It should be noted that the methods, codes and systems including its preferred embodiments as outlined in the present document may be used stand-alone or in combination with the other methods, codes and systems disclosed in this document. In addition, the features outlined in the context of a system are also applicable to a corresponding method or code (and vice versa). Furthermore, all aspects of the methods, codes and systems outlined in the present document may be arbitrarily combined. In particular, the features of the claims may be combined with one another in an arbitrary manner.

The invention is explained below in an exemplary manner with reference to the accompanying drawing, wherein FIG. 1 shows a block diagram of an example device for generating a perfume or fragrance;

Figure 1:
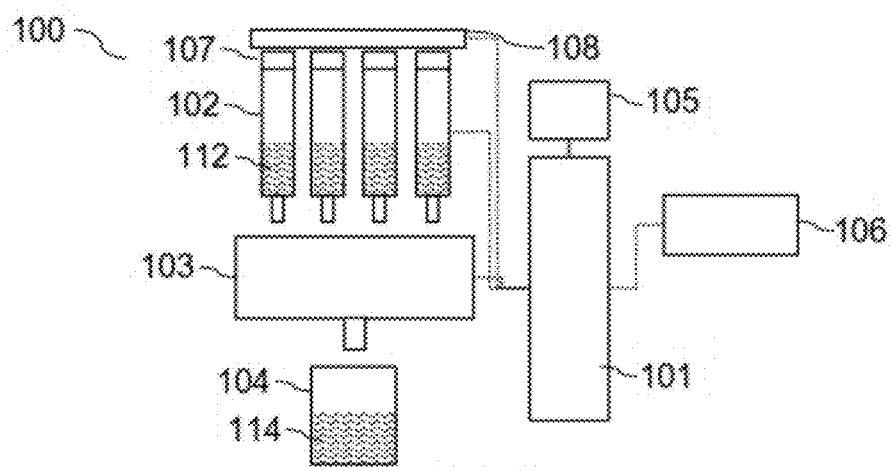

The present document relates to the technical problem of enabling a user to generate a perfume or fragrance in a comfortable and individualized manner. FIG. 1 shows a block diagram of an example perfume blender machine or device or system 100. The perfume blender machine 100 comprises a plurality of containers or cartridges 102 for different olfactory ingredients 112 (e.g. for different liquids with different scent or smell). A container or cartridge 102 comprises or may be coupled to dispensing means (e.g. a valve) for controlling the quantity of an ingredient which is provided into a mixing unit 103 or directly into a container 104 for the final perfume 114. Furthermore, the machine 100 comprises a control unit 101 which is configured to control the dispensing means of the containers 102, e.g. in dependence of a recipe fora perfume 114.

The machine 100 comprises a user interface 105 which enables a user to select or to compose a recipe for a perfume 114. Furthermore, the machine 100 may comprise or may be coupled to a communication unit 106 which is configured to interact with other parties (e.g. with a server within a network) via a communication network (e.g. a wireless network). The control unit 101 may be configured to determine a recipe for a perfume 114 (also referred to herein as an olfactory blend) via the communication unit 106.

A cartridge 102 for an olfactory ingredient 112 may comprise communication means 107 for providing information regarding the olfactory ingredient 112 that is comprised within the cartridge 102. The information may be provided to a reading unit 108 of the perfume blender machine 100. The communication means 107 may comprise a code (e.g. a QR code, a bar code, etc.), an RFID tag and/or an NFC chip. The information that is provided by the communication means 107 may comprise:
- information regarding the identity of the olfactory ingredient 112 comprised within the cartridge 102; in particular, an identifier of the olfactory ingredient 112; and/or
- information regarding the remaining quantity of the ingredient 112 within the cartridge 102.

The control unit 101 of a perfume blender machine 100 may be configured to collect the information provided by the plurality of cartridges 102 which are placed within the machine 100. In particular, the control unit 101 may be configured to determine which olfactory ingredients 112 (possibly including their respective quantities) are available for generating a perfume 114. Furthermore, the control unit 101 may be configured to determine a recipe for a perfume 114 which may be generated using the ingredients 112 that are available within the machine 100. For this purpose, the control unit 101 may download a recipe from a central server via the communication unit 106. In addition, the control unit 101 may be configured to control the perfume blender machine 100 to generate a certain portion (e.g. 5, 10 or 20 milliliters) of the perfume 114 using the recipe. For this purpose, the dispensing means may be controlled to dispense the quantities of the different ingredients 112 in accordance to the recipe.

Figure 2:
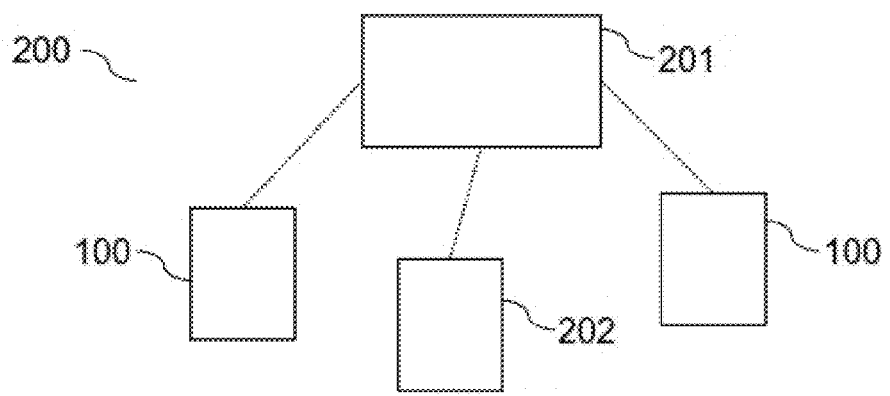
FIG. 2 shows an example system for exchanging information regarding perfumes or fragrances or olfactory ingredients.

FIG. 2 shows an example network 200 which may be used for exchanging information (e.g. recipes) regarding perfumes 114. The network 200 comprises a central server 201 which may hold a database for storing recipes for different perfumes 114. A recipe may indicate:
- the one or more olfactory ingredients 112 which are needed for generating a perfume 114; the one or more olfactory ingredients 112 may each be identified by a unique identifier; and/or
- the quantities of the one or more olfactory ingredients 112.

The recipes may be provided to the server 201 by different users. In particular, users may be enabled (e.g. using a web interface) to add recipes to the database that is stored on the server 201.

Various different perfume blender machines 100 and/or other electronic devices 202 (e.g. smartphones) may be enabled to communicate with the central server 201 and/or with one another. In particular, the network 200 may be used for exchanging information regarding recipes for perfumes 114 between different users.

As a basis for generating individualized perfumes 114, a standard set of olfactory ingredients 112 (comprising e.g. 100, 1000 or more different ingredients 112) may be provided. Each olfactory ingredient 112 of the standard set of ingredients 112 may be given a unique identifier. The unique identifier of an ingredient 112 may be encoded within the communication means 107 of a cartridge 102 which comprises this ingredient 112. The provision of a standard set of olfactory ingredients 112 enables the flexible creation of recipes for perfumes 114, such that the perfumes 114 are reproducible in a reliable manner.

Hence, a perfume blender machine 100 is described which uses cartridges 102 comprising different olfactory ingredients 112 (with different aromas or chords that are to be mixed). The machine 100 comprises a communication interface between the perfume blender machine 100 and the cartridges 102 (via the communication means 107 and the reader unit 108), in order to enable the machine 100 to identify the cartridges 102 which are connected to the machine 100.

The communication interface between the communications means 107 of a cartridge 102 and the reading unit 108 of the machine 100 may be configured to transmit information regarding the cartridge 102, even if the cartridge 102 is not placed within the machine 100. By way of example, the communication interface may have a certain communication range, which enables the machine 100 to identify the one or more cartridges 102 which are placed within the communication range (e.g. within the home of a user of the machine 100).

The communication interface between a cartridge 102 and a machine 100 may make use of graphic codes, e.g. a QR code, a data matrix, a bar code or any other suitable code. Alternatively or in addition, RFID communication or NFC communication may be used.

The communication between the cartridges 102 and the machine 100 provides e.g. the following functionalities:
- The machine 100 may determine the level of ingredients 112 comprised within the different cartridges 102.
- The machine 100 may determine the cartridges 102 (and corresponding ingredients 112) that are available within the machine 100 and/or within the communication range of the communication interface. This information may be used for making suggestions regarding a recipe for a perfume 114 that can be created using the available ingredients 112.
- The machine 100 may be configured to detect which cartridges 102 exhibit a relatively low filling level and to possibly place an order for purchasing one or more new cartridges 102.

Furthermore, the control unit 101 of the perfume blender machine 100 may be configured to determine the ingredients 112 (and their respective quantities) which have been used to generate a perfume 114 (e.g. based on instructions given by a user). This information may be summarized and/or encoded within a recipe which may be shared with other users (e.g. via a network 200). In particular, the control unit 101 may be configured to upload a recipe via the communication unit 106 to the recipe database of the server 201, in order to share the recipe with other users.

In an embodiment of a method for generating a fragrance 114 with a perfume blender machine 100 and a plurality of cartridges 102, the dispensing means of the machine may be controlled by the control unit 101 to generate a fragrance based on instructions inputted by the user on the liquid olfactory ingredients to be blended: which ingredients 112 or cartridges 102 have to be used, and which quantity of each ingredient has to be used.

The user may receive from the control unit 101 of the machine 100 the information regarding the available cartridges 102 or olfactory ingredients 112, e.g. through a screen or display on the machine 100, and may input instructions to the machine 100 through any suitable device such as a keyboard, touchpad, etc. provided on the machine itself. In other embodiments, the user may receive the information regarding the available cartridges 102 or olfactory ingredients 112, and/or may input instructions to the machine 100 via other means, such as a computer and/or mobile device, such as a smartphone, tablet, etc connected to the machine, either physically or through a wireless connection (wifi, Bluetooth, etc).

The control unit 101 of the machine 100 may record the information regarding the plurality of liquid olfactory ingredients and their respective quantities which have been blended in the fragrance 114, and generate a recipe of the fragrance 114 with the recorded information.

The control unit is configured to record the ingredients and the quantities used by the user to create a perfume, by identifying the ingredients inside each cartridge (i.e: RFID/NFC, QR; barcode or pictorial code reader), and by measuring by sensors or electronic means the volume of each cartridge dosed.

With the recorded information the control unit may generate a recipe for the new blend of ingredients, which results into a new fragrance created by the user. The recipe generated by the user may be recorded in the control unit of the device by means of embedded memory components in the electronic board of the control unit, such as: internal flash, external NAND flash, micro-SD cards, ROM or RAM.

The information stored by the control unit 101 of the perfume blender machine, may also or alternatively be transferred to a cloud network through the communication unit (106) of the device, or to a user mobile device or interface (105).

The recipe may be retrieved by the user, by means of the user interface (i.e: mobile device) or by accessing to the cloud, which will enable e.g. to share recipe with other users having other perfume blenders, to recreate the same fragrance, to create another on the base of the previous one, etc.

By providing a communication interface between cartridges 102 and perfume blender machines 100, a network 200 for creating and exchanging recipes is enabled. The communication means 107 of the cartridges 102 may be enabled to communicate with other electronic devices 202, such as smartphones. By doing this, a user is enabled to determine available olfactory ingredients 112 and corresponding recipes for perfumes 114 independently from a perfume blender machine 100. The information regarding the available olfactory ingredients 112 may be provided to a perfume blender machine 100, e.g. via the communication unit 106 of the perfume blender machine 100.

Figure 3:
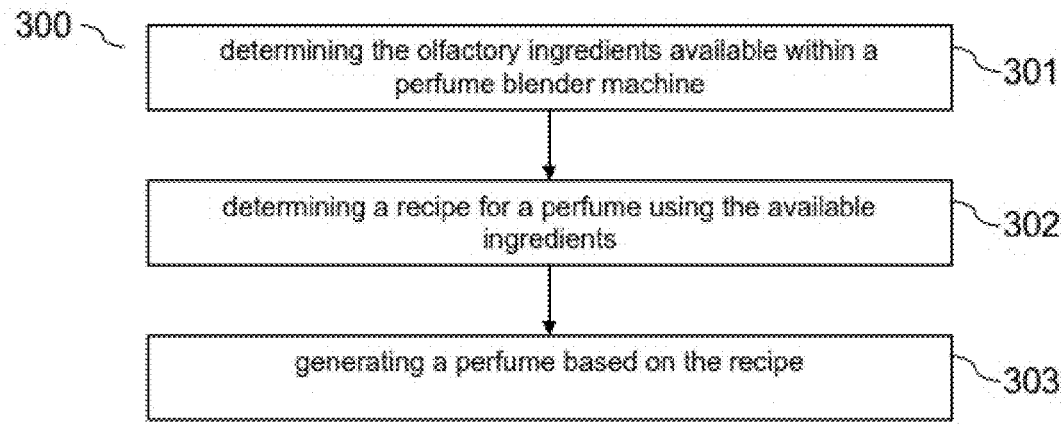
FIG. 3 shows a flow chart of an example method for generating an individualized perfume.

FIG. 3 shows a flow chart of a method 300 for generating a perfume or fragrance 114 within a perfume blender machine 100. The perfume blender machine 100 comprises a plurality of cartridges 102 for providing a corresponding plurality of olfactory ingredients 112. Furthermore, the perfume blender machine 100 comprises dispensing means configured to dispense one or more olfactory ingredients 112 from the plurality of cartridges 102 for generating a fragrance 114. In addition, the perfume blender machine 100 comprises reading means 108 which are configured to interact with the communication means 107 of the plurality of cartridges 102 for capturing information regarding the plurality of olfactory ingredients 112.

The method 300 comprises determining 301 information regarding the plurality of olfactory ingredients 112 comprised within the corresponding plurality of cartridges 102, based on the communication means 107 of the plurality of cartridges 102. Furthermore, the method 300 comprises determining a recipe for a fragrance or perfume 114, based on the information regarding the plurality of olfactory ingredients 112. In addition, the method 300 comprises generating the fragrance or perfume 114 based on the recipe.

In the present document, a network 200 for sharing information (notably recipes) regarding individualized perfumes 114 is described. Such a network 200 may include publicity, social gathering and any other reunion of people with smartphones 202 and/or perfume blender machines 100 that are enabled to communication with the communication means 107 of ingredient cartridges 102. Furthermore, the communication with the communication means 107 of ingredient cartridges 102 enables a perfume blender machine 100 to learn about the user preferences and to actively propose recipes for perfumes 114 based on the user preferences. Furthermore, a stock of available cartridges 102 may be tracked, new cartridges 102 may be purchased and/or recipes for perfumes 114 may be adapted to the available cartridges 102.

Figure 4:
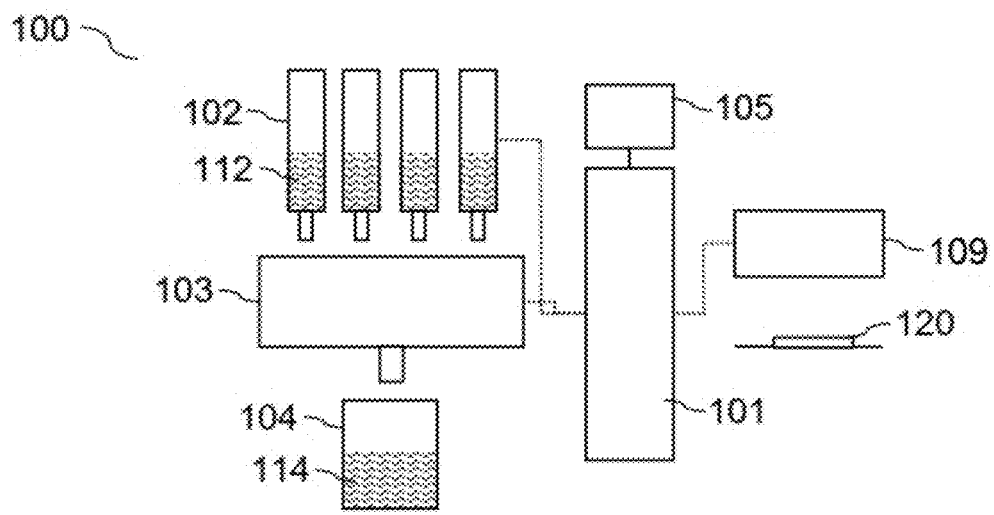
FIG. 4 shows a block diagram of an example system for generating a fragrance or perfume.

The present document further relates to the technical problem of enabling both, a user and a system (notably a perfume blender machine) to determine the composition of a perfume. The perfume may be produced within the perfume blender machine. In this context, FIG. 4 shows a block diagram of an example perfume blender machine 100. The perfume blender machine 100 comprises a plurality of containers 102, for example cartridges, for different olfactory ingredients 112 (e.g. for different liquids with different scent or smell). A container 102 comprises dispensing means (e.g. a valve) for controlling the quantity of an ingredient which is provided into a mixing unit 103 or directly to a container 104 for the final perfume 114. Furthermore, the machine 100 comprises a control unit 101 which is configured to control the dispensing means of the containers 102, e.g. in dependence of a recipe or a pictorial code 120 fora perfume 114.

The control unit of the perfume blender can read the pictorial code of cartridges and recipes.

The machine 100 comprises a user interface which enables a user to select or to compose a recipe for a perfume. Furthermore, the machine 100 may comprise or may be coupled to a camera 109 (e.g. coupled via Bluetooth or wifi to the camera of a mobile device, which may serve as user interface) which is configured to capture image data regarding a pictorial code 120 which describes the composition and/or the recipe of a perfume 114 (also referred to herein as an olfactory blend).

A perfume blender machine "B" can reproduce a recipe generated by the user of another perfume blender machine "A", by decoding the pictorial code shared by user of machine "A" with user of machine B.

With this purpose, user of machine "B" communicates to the control unit of perfume blender machine "B" the pictorial code of the recipe to replicate, by:

Downloading the pictorial code from a database into his user interface (i.e: mobile device) and sending the code e.g. via Bluetooth to the control unit.

Taking a picture of the pictorial code with the camera coupled to this mobile device, or a camera attached to the perfume blender system 109.

To enable a user and a perfume blender machine to determine the composition of an individual fragrance or perfume in a comfortable and precise manner, the user interface creates a pictorial code from the information stored about the recipe.

The pictorial code of a recipe (fragrance o perfume) is correlated with the pictorial code used to represent the composition of each cartridge used to create the individual fragrance or perfume (recipe).

This enables the user to:

Understand the properties and the function of the ingredient of each of the individual cartridges.

Understand and determine the properties of a final fragrance or perfume produced by the perfume blender device, resulting from the combination of different volumes or quantities of different ingredients, i.e. from different cartridges.

Figure 5:
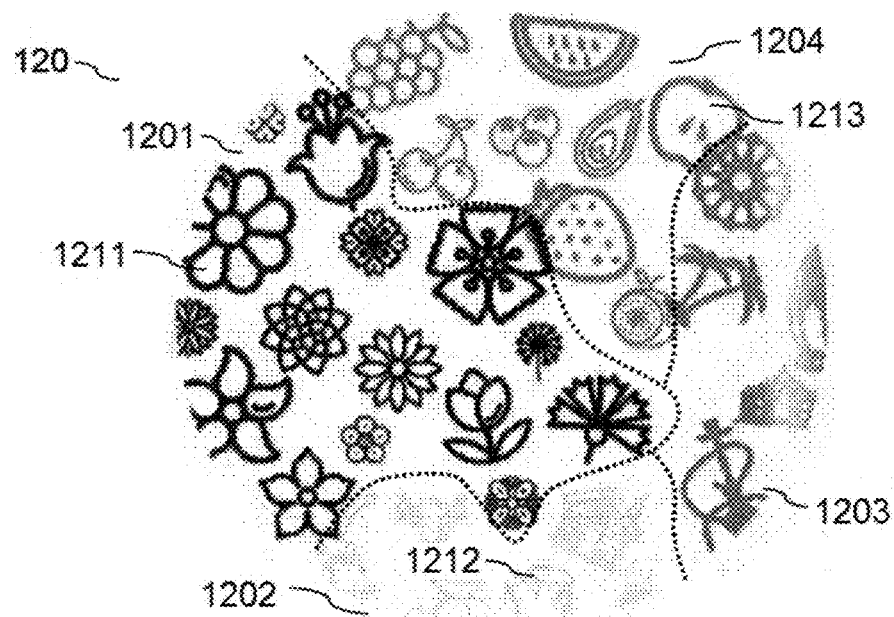
FIG. 5 shows an example pictorial code for describing the composition of a fragrance or perfume.

FIG. 5 shows an example embodiment of a pictorial code 120 for describing the composition of a perfume 114. The pictorial code 120 comprises one or more regions 1201, 1202, 1203, 1204 with different colours. In the illustrated example, the different regions 1201, 1202, 1203, 1204 are subdivided by dotted lines. These dotted lines are used herein for illustration purposes and may not actually be used within the pictorial code 120, as the different regions 1201, 1202, 1203, 1204 can typically be distinguished from one another based on the different colours.

The different colours may indicate different chords (also referred to as accords) of aromas (also referred to as notes). In particular, the different colours may indicate different categories of aromas. By way of example, the colour "brown" may be used to indicate wood aromas, the colour "yellow" may be used to indicate citric aromas, etc.

Furthermore, the pictorial code 120 comprises one or more different symbols or logos 1211, 1212, 1213. The symbols 1211, 1212, 1213 may be used to identify specific aromas or notes. The symbols 1211, 1212, 1213 may comprise or may be graphical representations of objects that are associated with specific aromas or notes. By way of example, a symbol 1211 indicating a flower may be indicative of a "flower" aroma, a symbol 1212 indicating a piece of wood may be indicative of a "wood" aroma and/or a symbol 1213 indicating an apple may be indicative of a "fruit" aroma, notably an "apple-type" aroma.

As such, the pictorial code 120 may describe the composition of a perfume 114 using differently coloured regions 1201, 1202, 1203, 1204, wherein the differently coloured regions 1201, 1202, 1203, 1204 comprise different symbols 1211, 1212, 1213. Such a code 120 may be read by the control unit 101 of a perfume blender machine 100 for determining the one or more ingredients 112, including the respective quantities, which are to be combined in order to generate a specific perfume 114. Furthermore, the pictorial code 120 may be read by a user in an intuitive manner, thereby providing the user with direct information regarding the composition and the scent or smell of the specific perfume 114.

Hence, a code 120 is described which comprises a combination of symbols or logos 1211, 1212, 1213 and colours. The colours may comprise information regarding the chords of aromas, e.g. brown for wood aromas, yellow for citric aromas, purple for floral aromas, etc. The colours may be assigned such that the colours are linked in the user's culture regarding the respective category of aromas. As such, the assignment between colours and chords or categories of aromas may be different for different countries and/or cultural groups.

The percentage of each colour within a code 120 may be indicative of the percentage of each chord within the olfactory blend 114.

Each chord may be made of or may comprise several individual aromas. The different aromas may be represented by different logos or symbols 1211, 1212, 1213. By way of example, a yellow region with a lemon and a lime may be indicative of a citric chord, wherein the citric chord comprises or is made up of lemon and lime.

In order to represent the percentage of each aroma within a chord, different characteristics of the logos 1211, 1212, 1213 may be adjusted:

the size of the logos 1211, 1212, 1213;

(relatively small) logos 1211, 1212, 1213 covering different areas of a coloured region;

an explicit numbers printed within the logos 1211, 1212, 1213;

etc.

In the example shown in FIG. 5 a code 120 for a perfume with four different chords is shown. A "purple" chord in region 1201 is dominant, followed by a red chord in region 1204, plus a relatively small green chord in region 1203 and a yellow chord in region 1202. The logos 1211, 1212, 1213 indicate that the purple chord is indicative of floral aromas, that the red chord is indicative of fruity aromas, that the yellow chord is indicative for wood aromas and the green chord is indicative for maritime aromas. Each chord comprises different aromas whose proportions are indicated using e.g. the size of each logo 1211, 1212, 1213. For example, the red chord with the fruity aromas comprises substantial amounts of strawberry and grape, but only relatively small amounts of avocado or tomato.

The camera 109 of the perfume blender machine 100 may be configured to capture a pictorial code 120, and the control unit 101 may be configured to decode the code 120, in order to determine the ingredients 112 and their quantities. Furthermore, a person is intuitively enabled to determine the components of the perfume 114 and the proportions between the different components using the pictorial code 120. The exact proportions may be determined using e.g. explicit numbers shown within the different logos 1211, 1212, 1213. Approximate proportions may be derived e.g. based on the size and/or numbers of the logos 1211, 1212, 1213.

The pictorial code 120 may be stored as a picture (e.g. within a smartphone of a user). Furthermore, the pictorial code 120 may be shared between different users, in order to exchange information regarding the composition of different perfumes 114.

Figure 6:
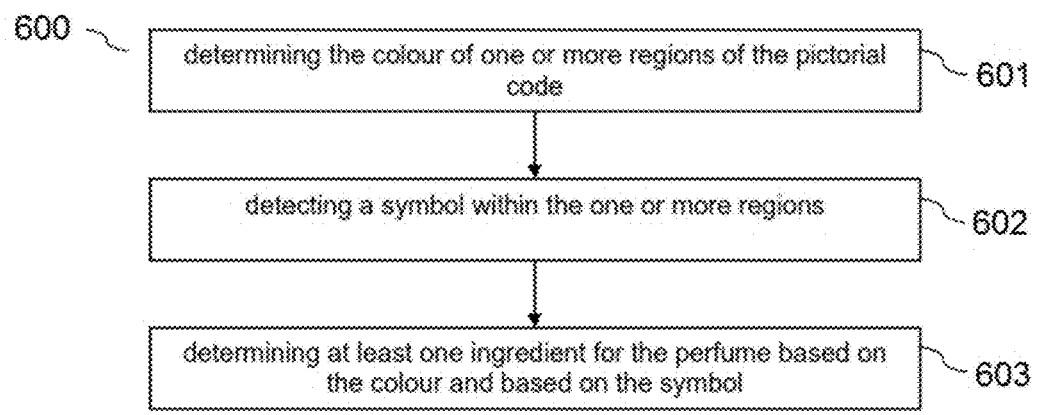
FIG. 6 shows a flow chart of an example method for determining the ingredients of a fragrance or perfume.

FIG. 6 shows a flow chart of an example method 600 for determining the composition of a perfume 114 from image date of a pictorial code 120. The image data may e.g. be captured by a camera 109 and/or the image data may be stored on a storage unit. The pictorial code 120 comprises one or more differently coloured regions 1201, 1202, 1203, 1204 and one or more symbols 1211, 1212, 1213 within the differently coloured regions 1201, 1202, 1203, 1204. In particular, the one or more symbols 1211, 1212, 1213 may have different colours, thereby defining the differently coloured regions 1201, 1202, 1203, 1204.

The method 600 comprises determining 601 the colour of the one or more differently coloured regions 1201, 1202, 1203, 1204 from the image data. In particular, it may be determined which one or more colours of a predetermined set of colours is comprised within the pictorial code 120. The set of colours may be associated or may correspond to a corresponding set of chord or accords of aromas. As such, the one or more colours comprised within a pictorial code 120 may be indicative of the chords or accords of aromas comprised within a perfume 114.

Furthermore, the method 600 comprises detecting 602 the one or more symbols 1211, 1212, 1213 based on the image data. The symbols 1211, 1212, 1213 may be placed within the differently coloured regions 1201, 1202, 1203, 1204. In particular, the symbols 1211, 1212, 1213 may have different colours. It may be determined which one or more symbols 1211, 1212, 1213 of a pre-determined set of symbols 1211, 1212, 1213 are comprised within the pictorial code 120. The set of symbols 1211, 1212, 1213 (notably in combination with different colours) may be associated with or may correspond to a set of different aromas. Hence, the symbols 1211, 1212, 1213 may be used to determine the specific aromas of a perfume 114.

The method 600 further comprises determining 603 at least one ingredient 112 of the perfume 114 based on the colour of the one or more differently coloured regions 1201, 1202, 1203, 1204 and based on the one or more symbols 1211, 1212, 1213. By way of example, a lookup table may comprise a first dimension for the different colours from a set of colours (e.g. N=5, 10 or more different colours). Furthermore, the lookup table may comprise a second dimension for the different symbols from a set of symbols (e.g. M=10, 20 or more symbols). As such, the lookup table may have N×M entries, wherein at least some (or all) of the entries may be associated with a particular olfactory ingredient 112. Hence, the pictorial code 120 may be used to indicate N×M different ingredients 112 from a set of ingredients 112 in a precise and intuitive manner.

Using the pictorial code 120 described in the present document, all relevant information regarding the composition of perfumes 114 can be shared between users. By way of example, a network may be provided, where users may share their olfactory creations. The pictorial code 120 allows encoding the exact formula of a perfume 114. At the same time, the pictorial code 120 enables a user to intuitively derive the (approximate) composition of a perfume 114.

It should be noted that the description and drawing merely illustrate the principles of the proposed methods and systems. Those skilled in the art will be able to implement various arrangements that, although not explicitly described or shown herein, embody the principles of the invention and are included within its spirit and scope. Furthermore, all examples and embodiment outlined in the present document are principally intended expressly to be only for explanatory purposes to help the reader in understanding the principles of the proposed methods and systems. Furthermore, all statements herein providing principles, aspects, and embodiments of the invention, as well as specific examples thereof, are intended to encompass equivalents thereof.

For reasons of completeness, various aspects of the invention are set out in the following numbered clauses:

Clause 1. A cartridge (102) for storing an olfactory ingredient (112) for a fragrance; wherein the cartridge (102) comprises communication means (107) configured to provide information regarding the olfactory ingredient (112) comprised within the cartridge (102) in a machine readable manner.

Clause 2. The cartridge (102) of clause 1, wherein the communication means (107) are configured to provide information regarding a level of the olfactory ingredient (112) comprised within the cartridge (102) in a machine readable manner.

Clause 3. The cartridge (102) of any previous clause, wherein information regarding the olfactory ingredient (112) comprises an identifier which is configured to identify the olfactory ingredient (112) from a pre-determined set of olfactory ingredients (112) in an unambiguous and/or bijective manner.

Clause 4. The cartridge (102) of any previous clause, wherein the communication means (107) comprise one or more of: a machine readable code, an RFID tag and/or an NFC chip.

Clause 5. The cartridge (102) of any previous clause, wherein the communication means (107) are configured to provide a wireless communication interface with a corresponding reading unit (108) over a communication range; wherein the communication rage is 1, 5 or more meters.

Clause 6. A system (100) configured to generate a fragrance (114); wherein the machine (100) comprises,
a plurality of cartridges (102) according to any of the previous clauses, for providing a corresponding plurality of olfactory ingredients (112);
dispensing means configured to dispense one or more olfactory ingredients (112) from the plurality of cartridges (102) for generating a fragrance (114);
reading means (108) configured to interact with the communication means (107) of the plurality of cartridges (102) for capturing information regarding the plurality of olfactory ingredients (112); and
a control unit (101) configured to
determine the information regarding the plurality of olfactory ingredients (112); determine a recipe for a fragrance (114) based on the information regarding the plurality of olfactory ingredients (112); and
control the dispensing means to generate the fragrance (114) based on the recipe.

Clause 7. The system (100) of clause 6, wherein the control unit (101) is configured to determine identifiers for the plurality of olfactory ingredients (112); and search for an appropriate recipe within a recipe database using the identifiers.

Clause 8. The system (100) of any of clauses 6 to 7, wherein the control unit (101) is configured to communicate with an external server (201) via a communication unit (106) of the system (100) for determining the recipe for the fragrance (114).

Clause 9. The system (100) of any of clauses 6 to 8, wherein
the reading means (108) exhibit a communication range for capturing data from the communication means (107) of a cartridge (102);
the communication range goes beyond a dimension of the system (100);
the control unit (101) is configured to determine additional information regarding an additional olfactory ingredient (112) comprised in one or more cartridges (102) that are not placed within the system (100); and
the control unit (101) is configured to determine a proposal for a recipe based on the additional information.

Clause 10. An electronic device (202) configured to determine information regarding an olfactory ingredient (112) of a cartridge (102) according to any of clauses 1 to 5; wherein the electronic device (202) comprises,
reading means (108) configured to interact with the communication means (107) of the cartridge (102) for determining an identifier of the olfactory ingredient (112); and a communication unit (106) configured to communicate with an external server (201) in order to determine information regarding the olfactory ingredient (112) based on the identifier.

Clause 11. A server (201) comprising a recipe database storing recipes for fragrances (114); wherein the server (201) is configured to
receive a request for a recipe from an electronic device (202) or from a system (100) for generating a fragrance (114); wherein the request comprises an identifier of one or more olfactory ingredients (112); and
identify one or more recipes from the recipe database based on the request; and send information regarding the one or more recipes to the electronic device (202) or to the system (100) for generating a fragrance (114).

Clause 12. A method (600) for determining the composition of a fragrance or perfume (114) from image date of a pictorial code (120); wherein the pictorial code (120) comprises one or more differently coloured regions (1201, 1202, 1203, 1204) and one or more symbols (1211, 1212, 1213) within the differently coloured regions (1201, 1202, 1203, 1204); wherein the method (600) comprises
determining (601) the colour of the one or more differently coloured regions (1201, 1202, 1203, 1204) from the image data;
detecting (602) the one or more symbols (1211, 1212, 1213) based on the image data; and
determining (603) at least one ingredient (112) of the fragrance or perfume (114) based on the colour of the one or more differently coloured regions (1201, 1202, 1203, 1204) and based on the one or more symbols (1211, 1212, 1213).

Clause 13. The method (600) of clause 12, further comprising
determining, based on the image data, relative sizes of the one or more differently coloured regions (1201, 1202, 1203, 1204) within the pictorial code (120); and
determining a quantity of the at least one ingredient (112) based on the relative sizes of the one or more differently coloured regions (1201, 1202, 1203, 1204).

Clause 14. The method (600) of any previous clauses, further comprising
determining, based on the image data, a characteristic of a symbol (1211, 1212, 1213); wherein the characteristic comprises a size, a quantity and/or a position within the pictorial code (120); and
determining a quantity of the at least one ingredient (112) based on the characteristic of the symbol (1211, 1212, 1213).

Clause 15. The method (600) of any previous clauses, wherein
a colour of a region (1201, 1202, 1203, 1204) is indicative of a chord, an accord or a category of aromas or notes; and
a symbol (1211, 1212, 1213) is indicative of an aroma or a note.

Clause 16. The method (600) of any previous clauses, wherein determining (603) at least one ingredient (112) comprises selecting an ingredient (112) from a pre-determined set of ingredients (112).

Clause 17. A pictorial code (120) for describing the composition of a fragrance or perfume (114) comprising one or more olfactory ingredients (112); wherein the pictorial code (120) comprises
one or more differently coloured regions (1201, 1202, 1203, 1204); and
one or more symbols (1211, 1212, 1213) within the differently coloured regions (1201, 1202, 1203, 1204); wherein the colour of the one or more differently coloured regions (1201, 1202, 1203, 1204) and the one or more symbols (1211, 1212, 1213) are indicative of the one or more olfactory ingredients (112) of the fragrance or perfume (114).

Clause 18. The pictorial code (120) of clause 17, wherein the pictorial code (120) exhibits a total size; and
a relative size of the one or more differently coloured regions (1201, 1202, 1203, 1204) is indicative of a quantity of the one or more olfactory ingredients (112) of the fragrance or perfume (114).

Clause 19. The pictorial code (120) of any of clauses 17 or 18, wherein
a symbol (1211, 1212, 1213) of the pictorial code (120) comprises a pictorial representation of an object which is associated with a particular scent or smell; and the one or more olfactory ingredients (112) of the fragrance or perfume (114) that is described by the pictorial code (120) comprise at least one olfactory ingredient (112) with the particular scent or smell.

Clause 20. The pictorial code (120) of any of clauses 17 to 19, wherein
the pictorial code (120) comprises a number field associated with a first symbol (1211, 1212, 1213) of the one or more symbols (1211, 1212, 1213); and
the number field is indicative of a quantity of a first olfactory ingredient (112) of the one or more olfactory ingredients (112) of the fragrance or perfume (114); and the first olfactory ingredient (112) is associated with the first symbol (1211, 1212, 1213).

Clause 21. A system (100) for generating a fragrance or perfume (114) from a set of olfactory ingredients (112); wherein the system (100) comprises
a plurality of containers (102) for a corresponding plurality of olfactory ingredients (112);
dispensing means configured to dispense one or more olfactory ingredients (112) from the plurality of containers (102) for generating a fragrance or perfume (114); and
a control unit (101) configured to
determine image data of a pictorial code (120) describing the composition of a fragrance or perfume (114);
determine the colour of one or more differently coloured regions (1201, 1202, 1203, 1204) of the pictorial code (120), based on the image data;
detect one or more symbols (1211, 1212, 1213) represented within the pictorial code (120), based on the image data;
determine at least one ingredient (112) from the plurality of ingredients (112), based on the colour of the one or more differently coloured regions (1201, 1202, 1203, 1204) and based on the one or more symbols (1211, 1212, 1213); and
control the dispensing means to dispense the at least one ingredient (112) from the corresponding at least one container (102) of the system (100).

The invention claimed is:
1. A method for generating a fragrance, comprising:
providing a perfume blender machine and a plurality of cartridges for storing a corresponding plurality of liquid olfactory ingredients, the perfume blender machine comprising dispensing means configured to dispense one or more olfactory ingredients from the plurality of cartridges for generating a fragrance;

controlling, via a control unit, the dispensing means to generate a fragrance based on instructions inputted by a user on the liquid olfactory ingredients to be blended and the quantity of each;

recording, via the control unit, the instructions inputted by the user and corresponding information regarding the plurality of liquid olfactory ingredients and their respective quantities which have been used to generate the fragrance, the recording comprises:

generating and storing a pictorial code representing the composition of the fragrance, and generating and storing a machine readable code associated with the pictorial code, wherein the pictorial code has one or more differently colored regions and one or more symbols within the colored regions, the color of the one or more differently colored regions and the one or more symbol are indicative of the one or more olfactory ingredients of the fragrance, the pictorial code exhibits a total size, and a relative size of the one or more differently colored regions is indicative of a quantity of the one or more olfactory ingredients of the fragrance; and generating a recipe of the fragrance with the recorded information.

2. The method as claimed in claim 1, comprising uploading the recipe via a communication unit of the perfume blender machine to a recipe database of a server in order to share the recipe with other users.

3. The method as claimed in claim 1, wherein a set of instructions inputted to the perfume blender machine by a user is recorded by a control unit of the perfume blender machine.

4. The method as claimed in claim 1, comprising loading a recipe of a fragrance in a memory of a user mobile device, allowing the user to modify the recipe by adding ingredients, removing ingredients, and/or altering the quantities of each ingredient, and controlling the dispensing means to generate a fragrance based on the modified recipe.

5. A method for generating a fragrance, comprising:

providing a perfume blender machine, comprising:

a plurality of cartridges for storing a corresponding plurality of liquid olfactory ingredients and provided with communication means configured to provide information regarding the olfactory ingredient comprised within the cartridge in a machine readable manner;

dispensing means configured to dispense one or more olfactory ingredients from the plurality of cartridges for generating a fragrance;

reading means configured to interact with the communication means of the plurality of cartridges for capturing information regarding the plurality of olfactory ingredients; and a control unit;

determining, via the control unit, the information regarding the plurality of olfactory ingredients;

determining, via the control unit, a recipe for a fragrance based on the information regarding the plurality of liquid olfactory ingredients and their respective quantities, and based on instructions given by a user;

controlling, via the control unit, the dispensing means to generate the fragrance based on the recipe; and encoding within the recipe, via the control unit, the information regarding the plurality of liquid olfactory ingredients and their respective quantities which have been used to generate the fragrance, the encoding within the recipe the information regarding the plurality of liquid olfactory ingredients and their respective quantities which have been used to generate the fragrance comprises:

generating and storing a pictorial code representing the composition of the fragrance, and generating and storing a machine readable code associated with the pictorial code, wherein the pictorial code has one or more differently colored regions and one or more symbols within the colored regions, the color of the one or more differently colored regions and the one or more symbol are indicative of the one or more olfactory ingredients of the fragrance, the pictorial code exhibits a total size, and a relative size of the one or more differently colored regions is indicative of a quantity of the one or more olfactory ingredients of the fragrance.

6. The method as claimed in claim 5, comprising uploading the recipe via a communication unit of the perfume blender machine to a recipe database of a server in order to share the recipe with other users.

7. The method as claimed in claim 5, wherein to determine the recipe for the fragrance the control unit of the perfume blender machine records a set of instructions inputted to the perfume blender machine by a user.

8. The method as claimed in claim 5, wherein to determine the recipe for the fragrance the control unit of the perfume blender machine detects and records the cartridges used and the corresponding quantity of liquid olfactory ingredient dispensed from each cartridge by the dispensing means following the instructions given by a user.

9. The method as claimed in claim 8, wherein the control unit of the perfume blender machine detects the quantity of liquid olfactory ingredient dispensed from each cartridge by the dispensing means through sensors.

10. The method as claimed in claim 5, further comprising retrieving the stored recipe with a mobile device in order to share the recipe with other users.

* * * * *